US012773151B2

(12) United States Patent
Anand et al.

(10) Patent No.: US 12,773,151 B2
(45) Date of Patent: Oct. 27, 2026

(54) APPARATUS AND METHOD FOR DETERMINING A NORMALIZED VOLTAGE ACROSS NON-IDENTICAL ELECTRODES

(71) Applicant: Anumana, Inc., Cambridge, MA (US)

(72) Inventors: Deepak Anand, Bangalore (IN); Yogisha Heggadahalli Jayendra, Bengaluru (IN); Karthik K. Bharadwaj, Bengaluru (IN); Sughosh Indurkar, Bangalore (IN); Rakesh Barve, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/911,857

(22) Filed: Oct. 23, 2024

(65) Prior Publication Data

US 2026/0108197 A1 Apr. 23, 2026

(51) Int. Cl.
*A61B 5/313* (2021.01)
*A61B 5/00* (2006.01)

(52) U.S. Cl.
CPC ............ *A61B 5/313* (2021.01); *A61B 5/7257* (2013.01); *A61B 5/7267* (2013.01)

(58) Field of Classification Search
CPC ..... A61B 5/313; A61B 5/7257; A61B 5/7267; A61B 5/7253
See application file for complete search history.

(56) References Cited

U.S. PATENT DOCUMENTS 11,147,496 B2 10/2021 Ghodrati et al.
2012/0172702 A1* 7/2012 Koyrakh .............. A61B 5/7267 600/408
2020/0337647 A1* 10/2020 Chen ...................... A61B 5/021
2021/0259633 A1 8/2021 Visweswara et al.
2021/0315639 A1 10/2021 Manucherhabadi et al.
2022/0238218 A1* 7/2022 Eliyahu ................ A61B 5/7267
2024/0090776 A1* 3/2024 Jang ........................ A61B 5/086
2024/0277285 A1* 8/2024 Souayah ................ A61B 5/262
2025/0082227 A1* 3/2025 Shi .......................... G06F 3/017

FOREIGN PATENT DOCUMENTS

CN 106321085 A 1/2017
KR 20180104454 A 9/2018

* cited by examiner

*Primary Examiner* — Justin Xu
*Assistant Examiner* — Jonathan M Haney
(74) *Attorney, Agent, or Firm* — CALDWELL LLC

(57) ABSTRACT

An apparatus and method for determining a normalized voltage across non-identical electrodes. The apparatus includes a first transducer having a first electrode type and configured to detect bioelectrical activity and output a first potential signal, as a function of the bioelectrical activity and at least a processor and a memory communicatively connected to the at least a processor. The memory instructs the processor to receive the first potential signal, and to generate, using a normalization model, a normalized potential signal as a function of the first potential signal, wherein generating the normalized potential signal comprises generating the normalization model comprises training the normalization model using paired potential signal data, wherein the paired potential signal data comprises first potential signal data collected from a first electrode type paired with second potential signal data collected from a second electrode type.

20 Claims, 10 Drawing Sheets

APPARATUS AND METHOD FOR DETERMINING A NORMALIZED VOLTAGE ACROSS NON-IDENTICAL ELECTRODES

FIELD OF THE INVENTION

The present invention generally relates to the field of electrophysiology. In particular, the present invention is directed to an apparatus and a method for determining a normalized voltage across non-identical electrodes.

BACKGROUND

In various fields, such as electrochemistry and biomedical devices, non-identical electrodes are commonly used, differing in size, material, or geometry. These differences can introduce significant challenges in obtaining consistent voltage measurements, as each electrode can exhibit distinct electrical properties that skew results. Traditional measurement methods are generally designed for identical or nearly identical electrodes, making them unsuitable for systems with non-identical electrodes. This mismatch can lead to unreliable data, affecting the accuracy and reliability of critical processes.

SUMMARY OF THE DISCLOSURE

In an aspect, an apparatus for determining a normalized voltage across non-identical electrodes includes a first transducer having a first electrode type and configured to detect bioelectrical activity and output a first potential signal, as a function of the bioelectrical activity and at least a processor and a memory communicatively connected to the at least a processor. The memory contains instructions configuring the processor to receive, using the at least a processor, the first potential signal from a first transducer of a plurality of transducers, and generate, using a normalization model, a normalized potential signal as a function of the first potential signal, wherein generating the normalized potential signal comprises generating the normalization model comprises training the normalization model using paired potential signal data, wherein the paired potential signal data comprises first potential signal data collected from a first electrode type paired with second potential signal data collected from a second electrode type, wherein each pair of first potential signal data and second potential signal data were collected at the same location.

In another aspect, a method for determining a normalized voltage across non-identical electrodes includes receiving, using the at least a processor, a first potential signal from a first transducer of a plurality of transducers, and generating, using a normalization model, a normalized potential signal as a function of the first potential signal, wherein generating the normalized potential signal comprises generating the normalization model comprises training the normalization model using paired potential signal data, wherein the paired potential signal data comprises first potential signal data collected from a first electrode type paired with second potential signal data collected from a second electrode type, wherein each pair of first potential signal data and second potential signal data were collected at the same location.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

At a high level, aspects of the present disclosure are directed to apparatus and methods for determining a normalized voltage across non-identical electrodes. The apparatus includes a first transducer having a first electrode type and configured to detect bioelectrical activity and output a first potential signal, as a function of the bioelectrical activity and at least a computing device comprised of a processor and a memory communicatively connected to the processor. The memory instructs the processor to receive the first potential signal from a first transducer of a plurality of transducers. The memory then instructs the processor to generate, using a normalization model, a normalized potential signal as a function of the first potential signal, wherein generating the normalized potential signal comprises generating the normalization model comprises training the normalization model using paired potential signal data, wherein the paired potential signal data comprises first potential signal data collected from a first electrode type paired with second potential signal data collected from a second electrode type, wherein each pair of first potential signal data and second potential signal data were collected at the same location.

Figure 1:
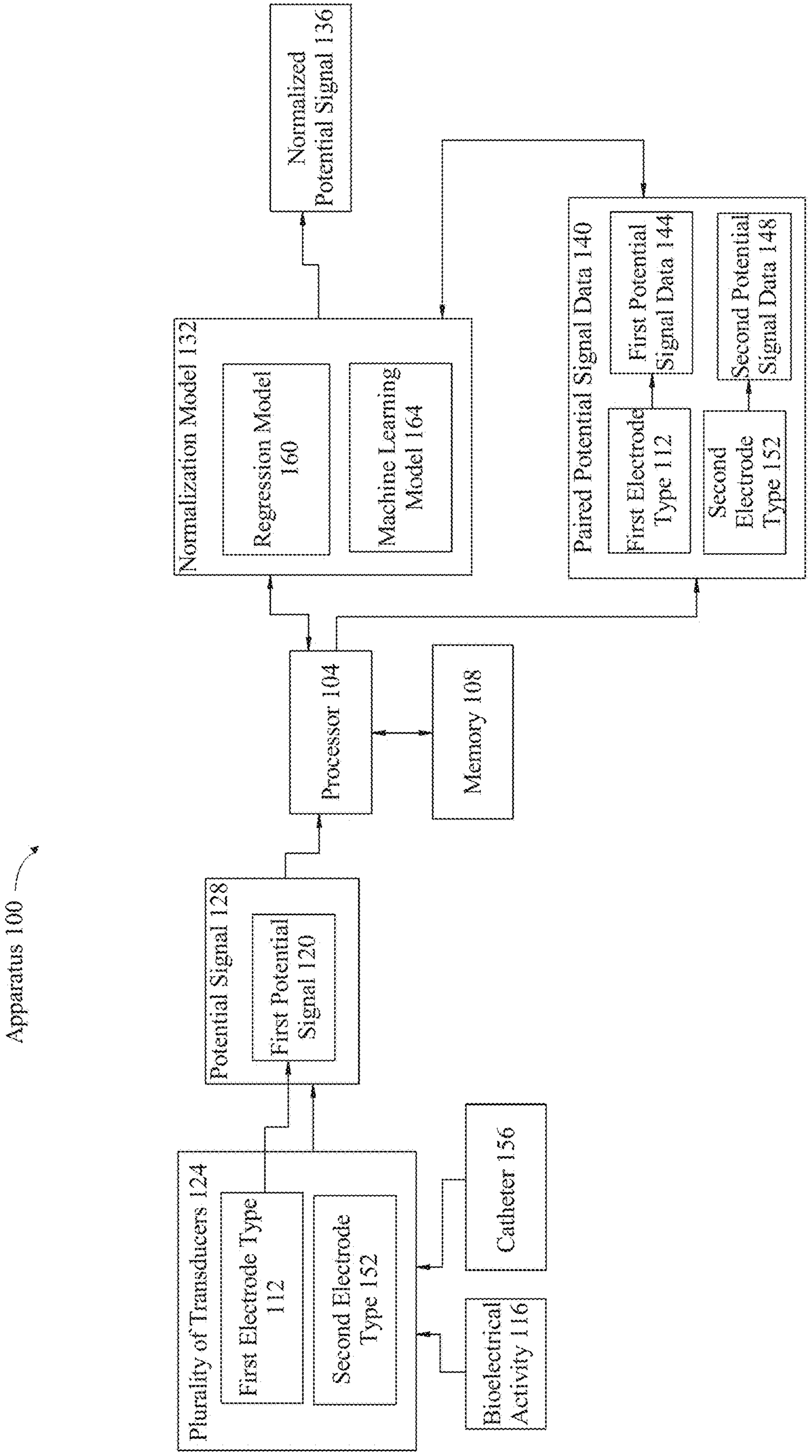
FIG. 1 is a block diagram of an apparatus for determining a normalized voltage across non-identical electrodes.

Referring now to FIG. 1, an exemplary embodiment of apparatus 100 for determining a normalized voltage across non-identical electrodes is illustrated. Apparatus 100 may include a processor 104 communicatively connected to a memory 108. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 104 may access the information from primary memory.

Still referring to FIG. 1, apparatus 100 may include a database. The database may include a remote database. The database may be implemented, without limitation, as a relational database, a key-value retrieval database such as a NOSQL database, or any other format or structure for use as database that a person skilled in the art would recognize as suitable upon review of the entirety of this disclosure. The database may alternatively or additionally be implemented using a distributed data storage protocol and/or data structure, such as a distributed hash table or the like. The database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, apparatus 100 may include and/or be communicatively connected to a server, such as but not limited to, a remote server, a cloud server, a network server and the like. In one or more embodiments, the computing device may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by the apparatus computing device. In one or more embodiments, computing device may transmit processes to server wherein computing device may conserve power or energy.

Further referring to FIG. 1, apparatus 100 may include any "computing device" as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing devices operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, the apparatus includes a first transducer having a first electrode type 112 and configured to detect bioelectrical activity 116 and output a first potential signal 120, as a function of the bioelectrical activity 116. As used in this disclosure, "bioelectrical activity" is the electrical phenomena generated by living tissues, organs, or cells as a result of their physiological functions. Without limitation, bioelectrical activity 116 may result from the movement of ions across cell membranes which yield changes in electrical potential. Continuing, bioelectrical activity 116 may be observed in various biological systems, such as in neurons (neural activity), muscles (muscular contractions), cardiac tissues (heart rhythms), and the like. As used in this disclosure, a "potential signal" is the electrical signal generated and output by a transducer in response to detecting physiological phenomena. In a non-limiting example, the physiological phenomena may be detected within biological tissues, organs, systems, and the like. Without limitation, the potential signal 128 may be indicative of various forms of electrical activity. For instance, the electrical activity may arise from cardiac, neural, or muscular functions. In a non-limiting example, a potential signal 128 may be generated by a transducer embedded in at least a catheter 156 during an electrophysiological study. Continuing, when the catheter 156 is positioned within a specific tissue, such as intracardially, the transducer may detect electrical impulses corresponding to the depolarization and repolarization phases of the cardiac cycle. Similarly, the transducer may detect neural activity such as the electrical impulses that arise when neurons fire.

With continued reference to FIG. 1, for the purposes of this disclosure, a "transducer" is a device used to transform one kind of energy into another. A measurable quantity of energy may include sound pressure, optical intensity, magnetic field intensity, thermal pressure, etc. When a transducer converts an electrical signal into another form of energy such as sound, light, mechanical movement, it may be called an actuator. It should be noted that sound is incidentally a pressure field. Actuators allow the use of feedback at the source of the measurements.

With continued reference to FIG. 1, a sensor may be considered as a component or with a collection of electronics such as amplifiers, decoders, filters, computer devices and apparatus 100. For the purposes of this disclosure an "instrument" is a sensor bundled with its associated electronics. However, in some embodiments, sensors may be further integrated with apparatus 100.including first transducer and at least a computing device.

With continued reference to FIG. 1, a sensor integrated with apparatus 100 may be linear so that response y to a stimulus x is in the form: $y(x)=Ax$, $0 \leq x \leq x_{max}$, $A>0$. It should be noted, there is a presumption that the stimulus to be positive. A is the sensitivity of the transducer gain, or the gain of the sensor. The gain is presumed to be positive for which the linear model satisfies the definition of linearity: $y(x+z)=A\ (x+z)=y(x)+y(z)$. It should be noted that this example is an idealized form of a sensor and may extend beyond the linearity constraints which may include time dependency, memory, and its output keeping track of input. A more generalized sensor may include the steady state transfer function of the sensor. For this case, the sensitivity can be defined as the derivative of the output with respect to the input:

$$S = \frac{\partial y}{\partial x}.$$

In this example, the sensor exhibits sensitivities to other operating parameters (i.e. supply voltage) or temperature. For the purposes of this disclosure, "sensitivity" is the ratio of output to input. This can include electrical output and signal input or an input transducer. It can also include physical output to an electrical input, or an output transducer. Sensitivity can also be used in its usual electrical meaning. In this it would refer to a percent change of a property of a device because of a percent change in a parameter. In some embodiments this would be a percent change in gain as a result of percent change in ambient temperature. This type of sensitivity may be referred to as the Gain of a sensor.

Still referring to FIG. 1, apparatus 100 with integrated sensors may not respond to arbitrarily small signals. Apparatus 100 may respond to signals within a specified range from zero to a sensor threshold which does not cause the output of the sensor to change. The existence of a threshold relates to the nonlinear behavior of the device and the noise. Apparatus 100 with an integrated sensor may fail to respond to stimuli which are arbitrarily large as well. In this case, apparatus 100 integrated with a sensor may have a max range. The full range of apparatus 100 integrated with a sensor may be limited by compression or clipping. Compression and clipping are results of nonlinearity and thus may include apparatus 100 as a nonlinearity device.

Still referring to FIG. 1, referring to the linear equation above assuming a linear sensor is improved with the addition of a constant: $y(x)=b_0+Ax$. It should be noted that the equation is not linear even though it is described as a first order polynomial. The constant is called a zero offset and can be defined in two ways: a sensor reading when the input is zero, or the value of the stimulus required to make the output zero. The zero offset is corrected by subtracting $b_0$ from y and recovering the linear description of a sensor: $y'(x)=y(x)-b_0=Ax$.

With continued reference to FIG. 1, apparatus 100 may include very fast measurements where it can internally store energy. Apparatus 100 output may depend on previous measurements the integrated sensors make. It should be noted that the sensor may exhibit memory. The time dependence of a sensor can be linear if the response is described by a linear differential equation:

$$\sum_{n=0}^{N} A_n \frac{\partial^n y}{\partial t^n} = \sum_{k=0}^{k} B_k \frac{\partial^k x}{\partial t^k}.$$

Taking the Laplace transform of this equation:

$$y(s, X) = \left( \frac{\sum_{k=0}^{K} B_k S^k}{\sum_{n=0}^{N} A_n S^n} \right) x = H(s)X(s),$$

which is in Laplace transform space and the sensor response is still linear in stimulus x. The response of a sensor with a transfer function H(s) at time t is the convolution integral between the history of the stimulus x and the inverse Laplace transform h(t) of H(s):

$$y(t) = \int_0^\infty h(\tau)x(t-\tau)d\tau.$$

Apparatus 100 may behave like a low pass filter, wherein there is a delayed response to their input. There is a limit to the maximum stimulus frequency that can be detected. The maximum frequency a sensor can interpret is approximately the inverse of its response time.

With continued reference to FIG. 1, as used in this disclosure, an "electrode" is a conductive element that facilitates the transmission or detection of electrical signals. Without limitation, an electrode may be used to measure bioelectrical activity 116, stimulate tissues, enable electrical current flow, and the like. In a non-limiting example, transducer may include one or more electrodes. In a non-limiting example, a single transducer may incorporate different types of electrodes. In a non-limiting example, the electrode may be placed on the surface of the skin or inserted into tissues. Without limitation, the electrodes may vary in size, shape, or material. For example, without limitation, electrodes may be designed to be larger or smaller depending on the area of contact required or the sensitivity of the measurements needed. Continuing, the electrode shape may be tailored for specific anatomical locations and/or to enhance conductivity. Additionally and or alternatively, the material used for the electrodes may differ based on factors such as biocompatibility, conductivity, durability, and the like. For instance, electrodes may be made from metals such as silver, gold, platinum, stainless steel, and the like. Without limitation, the aforementioned metals may be a conductive and durable material choice. Additionally and or alternatively, the electrodes may be made of silver/silver chloride (Ag/AgCl), polymers, carbon-based materials, and the like.

Figure 4:
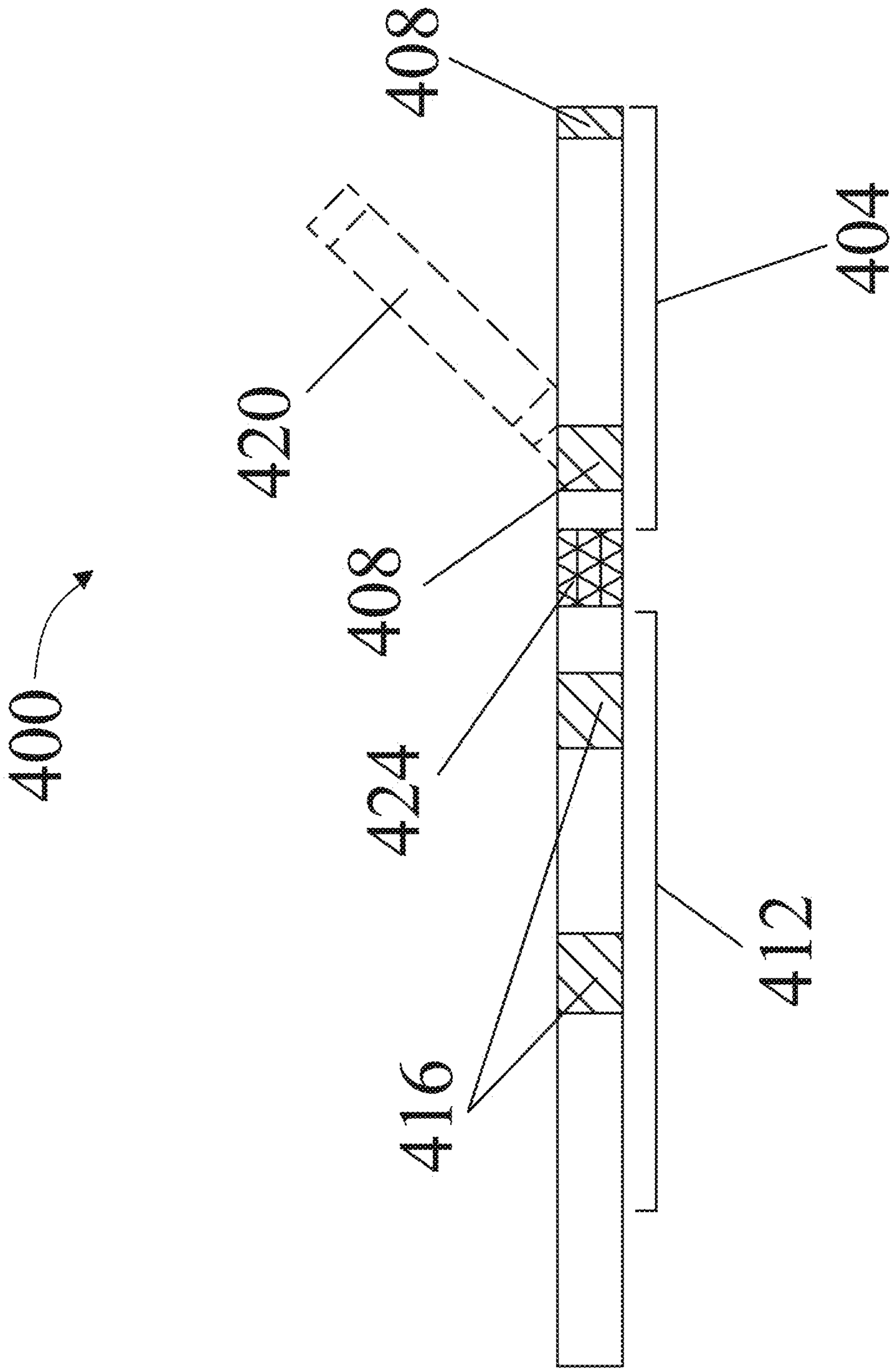
FIG. 4 is an illustration of a diagram of a transducer with a rigid part, a flexible part, a magnetic sensor, a first electrode type, and a second electrode type.

With continued reference to FIG. 1, as used in this disclosure, a "rigid electrode" is an electrode made from a solid, inflexible material that maintains its shape and structure during use. As used in this disclosure, a "non-rigid electrode" is an electrode made from materials that allow it to bend, stretch, or conform to irregular surfaces without losing its functionality. In a non-limiting example, the transducer may include both a rigid electrode and a non-rigid electrode in its design. Without limitation, the rigid part of the transducer may include a rigid electrode made from materials like stainless steel or platinum, providing a stable and durable contact point for deeper or more permanent implantation. Continuing, the rigid electrode may provide precise signal detection in environments where mechanical stability is crucial. Conversely, the transducer may also include a flexible portion that includes one or more non-rigid electrodes. Without limitation, the non-rigid electrodes may be made from materials like conductive polymers and/or thin layers of flexible carbon compounds. Continuing, the non-rigid electrode may conform to the surface of softer tissues, such as skin or muscle, allowing for greater comfort and adaptability in areas that move or flex. Continuing, the combination of rigid and non-rigid sections in the transducer may enable it to perform in a variety of conditions, offering both durability in fixed locations and flexibility in dynamic environments where movement or contouring is required. Refer to FIG. 4, FIG. 5A and FIG. B for exemplary illustrations of a transducer with both a rigid electrode and a non-rigid electrode.

Still referring to FIG. 1, processor 104 receives the first potential signal 120 from a first transducer of a plurality of transducers 124. The first electrode type 112 may include a surface electrode. As used in this disclosure, a "surface electrode" is a type of electrode placed on the skin to detect or deliver electrical signals from underlying tissues. Without limitation, surface electrodes may be non-invasive and used to measure bioelectrical activity 116 from the body's surface.

In another non-limiting example, the first electrode type 112 may include an intramuscular electrode. As used in this disclosure, an "intramuscular electrode" is a type of electrode inserted directly into a muscle to detect electrical activity within the muscle fibers. Without limitation, intramuscular electrodes may provide a more localized and precise measurements compared to surface electrodes.

With continued reference to FIG. 1, the plurality of transducers 124 may include various kinds of transducers such as electromyography (EMG) transducers for detecting muscle activity, electrocardiography (ECG) transducers for measuring heart signals, electroencephalography (EEG) transducers for recording brain activity, electroretinography (ERG) transducers for detecting retinal responses, electrogastrography (EGG) transducers for measuring stomach muscle activity, neural transducers for capturing signals from neurons, and the like. In a non-limiting example, the transducers may vary in shape, size, material composition, and the like. For instance, transducers may be small and compact for use in minimally invasive procedures or larger transducers in size for surface-level monitoring. Continuing, the shape of the transducers may range from flat and flexible for applications requiring skin contact to cylindrical or needle-like for insertion into tissues. Additionally and or alternatively, the material composition of the transducers may vary and include materials such as metals like stainless steel for durability, or polymers and flexible materials for lightweight, adaptable designs.

With continued reference to FIG. 1, the potential signal 128 may include electrogram (EGM) signals collected from the intramuscular electrode. As used in this disclosure, an "EGM signal" is an electrogram signal that represents the electrical activity recorded from muscles or organ systems. For instance, EGM signal may include the electrical activity recorded from the heart. In a non-limiting example, the EGM signal may be captured using electrodes placed inside or on the surface of the heart. Continuing, EGM signals may provide information about the heart's electrical conduction system. For instance, the EGM signal may provide information related to the timing and propagation of electrical impulses within the cardiac tissue. Continuing, the EGM signals may be used for diagnostic and monitoring purposes, such as in procedures related to arrhythmia detection, electrophysiological studies, and the like.

Still referring to FIG. 1, processor 104 generates, using a normalization model 132, a normalized potential signal 136 as a function of the first potential signal 120, wherein generating the normalized potential signal 128 comprises generating the normalization model 132 comprises training the normalization model 132 using paired potential signal data 140, wherein the paired potential signal data 140 includes first potential signal data 144 collected from a first electrode type 112 paired with second potential signal data 148 collected from a second electrode type 152, wherein each pair of first potential signal data 144 and second potential signal data 148 were collected at the same location. Without limitation, the "same location" refers to a spatial position within an acceptable variance. For instance, same location may be a location within 1%, 2%, 5%, 10%, 20%, 30%, 40&, or 50% variance between the locations where the first and second potential signal data were collected. In some cases, same location may refer to two locations within a positional tolerance of unilaterally or bilaterally within 0.5 mm, 1 mm, 3 mm, 5 mm, 10 mm, 20 mm, 30 mm, 40 mm, or 50 mm. In a non-limiting example, the slight variance provides for slight discrepancies due to practical limitations. Without limitation, the slight variance in location may ensure that the two signals represent the same general area.

With continued reference to FIG. 1, as used in this disclosure, a "normalization model" is an algorithm configured to adjust and standardize potential signals from non-identical electrodes. Without limitation, the normalization model 132 may account for variations in electrode properties, tissue contact, and the like, to provide an accurate comparison and analysis of the potential signals. As used in this disclosure, a "normalized potential signal" is an adjusted electrical signal that was processed using the normalization model 132. Without limitation, the normalized potential signal 136 may include the potential signal 128 from various electrodes that are converted into a single voltage. In a non-limiting example, the individual signals from each electrode may differ in amplitude or frequency due to differences in electrode properties or tissue contact. Continuing, the individual signals may be converted into a unified, standardized voltage. Continuing, this single voltage represents a harmonized signal that allows for accurate and consistent comparison across different electrodes, ensuring that any discrepancies in the raw data are minimized. Continuing, the output is a single, reliable voltage value that can be used for precise analysis, regardless of the type or configuration of the electrodes involved in the system. As used in this disclosure, "paired potential signal data" is a set of electrical signals collected from two or more electrodes. In a non-limiting example, the paired potential signal data 140 may be collected from the same location using two different types of electrodes. Continuing, the paired signal data may allow for a direct comparison and or analysis of relative differences. As used in this disclosure, a "first potential signal data" is electrical activity data collected from a first transducer wherein the first transducer includes a first type of electrode. For example, without limitation, the first potential signal data 144 may include the electrical activity from a bioelectrical transducer with a rigid electrode made of platinum. As used in this disclosure, a "first electrode type" is a specific type of electrode used to collect the first potential signal data 144. In a non-limiting example, the first electrode type 112 may differ from other electrode types in its unique characteristics such as size, shape, material composition, configuration, and/or the like. As used in this disclosure, a "second potential signal data" is electrical activity data collected from a second electrode type 152. For example, without limitation, the second potential signal data 148 may include the electrical activity from a bioelectrical transducer with a non-rigid electrode made of a polymer. As used in this disclosure, a "second electrode type" is a specific type of electrode used to collect the second potential signal data 148. In a non-limiting example, the second electrode type 152 may have different properties compared to the first electrode type 112, such as material, configuration, and/or function.

With continued reference to FIG. 1, the second electrode type 152 comprises an intramuscular electrode coupled to at least a catheter 156 configured for intramuscular use. As used in this disclosure, a "catheter" is a flexible tube inserted into the body to perform various medical procedures. In a non-limiting example, at least a catheter 156 may record and map at least a beat of cardiac phenomenon and output at least a visual element. In a non-limiting example, at least a catheter 156 may be used to facilitate the detection and mapping of cardiac activity, providing essential data for apparatus to process and analyze. In a non-limiting example, at least a catheter 156 may be used in procedures such as cardiac ablation or electrophysiological studies to gather detailed information about heart rhythms. Without limitation the second electrode type 152 may include an electrode made from a metal such as platinum, silver, gold, and/or stainless steel.

With continued reference to FIG. 1, the normalization model 132 comprises a regression model 160. As used in this disclosure, a "regression model" is a computational framework used to determine the relationships between a dependent variable and one or more independent variables. For instance, without limitation, the regression model 160 may analyze data to predict outcomes, assess trends, and/or make decisions by fitting a mathematical function to the observed data points. In a non-limiting example, the regression model 160 may be used to predict potential signals 128 based on electrode characteristics or physiological conditions. Without limitation, the regression model 160 may predict potential signals 128 by analyzing how various electrode characteristics, such as size, material, and placement, as well as physiological conditions, like tissue type or bioelectrical activity 116 levels, influence the output signal. Continuing, the regression model 160 may be trained on data from various electrode types and physiological readings to establish patterns or correlations between these factors and the resulting electrical signals. For instance, without limitation, the regression model 160 may predict how a change in electrode material affects signal amplitude or how differences in tissue conductivity influence signal quality.

With continued reference to FIG. 1, the paired potential signal data 140 may include Fast Fourier Transform (FFT) voltage data. As used in this disclosure, "FFT voltage data" is a transformed representation of time-domain voltage signals into the frequency domain using the Fast Fourier Transform algorithm. In a non-limiting example, the FFT voltage data may provide information into the frequency components of the voltage signals. For instance, without limitation, the FFT voltage data may provide a detailed analysis of the potential signal's spectral characteristics, such as identifying dominant frequencies, noise, or harmonics in bioelectrical signals. Continuing, the FFT voltage data may be used to analyze complex, periodic signals in applications like ECG or EGM to better understand their underlying patterns and behavior.

With continued reference to FIG. 1, the normalization model 132 may be configured to calculate a first FFT voltage value for a plurality of voltages of the first potential signal 120 across a plurality of frequencies of the first electrode type 112. As used in this disclosure, a "first FFT voltage value" is the result of applying the FFT to the first potential signal 120. In a non-limiting example, the first FFT voltage may represent the magnitude of the voltage at a specific frequency. In another non-limiting example, the first FFT voltage value may provide insight into the frequency-domain characteristics of the potential signal 128.

With continued reference to FIG. 1, the normalization model 132 may include a machine learning model 164. Without limitation, the machine learning model 164 may be trained using datasets of potential signals 128 collected from different electrode types, each with varying characteristics such as size, shape, material, and placement. Continuing, the machine learning model 164 may determine relationships and/or patterns among between these electrode variables and the corresponding potential signals 128. Continuing, the machine learning model 164 May predict the adjustments needed to normalize the potential signals 128 for accurate comparison and analysis. For instance, the machine learning model 164 may normalize signals from electrodes of varying materials, such as platinum or silver, to account for differences in conductivity, ensuring that the output signals are comparable across different systems. Continuing, the machine learning model 164 may continuously improve its accuracy by learning from real-time data predictions and user feedback thereby refining the normalization process for a wide range of potential signals 128 in applications such as diagnostics, monitoring, and/or research. Machine learning model 164 may be further described with respect to FIG. 6.

In a non-limiting example, normalization is to be derived once and then may be applied consistently. Without limitation, the normalization process may involve several steps to learn the transformation between different types of electrodes. First, multiple paired data points are collected at the exact same location using various types of electrodes. This ensures that the measurements are comparable across electrode types. Second, a transformation is learned, denoted as Θtype1→type2. Continuing, this transformation takes in the FFT voltages across all frequencies $$(V_i^{f1}, V_i^{f2}, \ldots, V_i^{fj}, \ldots V_i^{fm})$$

a type 1 electrode and uses a regression model to provide the corresponding FFT voltages for a type 2 electrode at the same location. Finally, the trained models may be used for real-time conversion of voltages across the various types of electrodes. Without limitation, once the voltages from all the electrodes have been converted to match a single type, all electrodes can be treated as identical, provided there are no significant variations in the field characteristics during data collection. Pictorially, the voltage normalization process is illustrated here: Voltage at electrode i of Type 1 at location x,y,z $$(V_i^{f1}, V_i^{f2}, \ldots, V_i^{fj}, \ldots V_i^{fm})_1$$

and Voltage at electrode i of Type 2 at the same location x, y, z $$(V_k^{f1}, V_k^{f2}, \ldots, V_k^{fj}, \ldots V_k^{fm})_2$$

because the types are different, even at the same x, y, z, location $$V_i^{fj} \mathrel{!=} V_k^{fj}$$

thus the Normalization Model:

$$\theta_{type1 \rightarrow types2}(V_i^{f1}, V_i^{f2}, \ldots, V_i^{fj}, \ldots V_i^{fm})_{original} \rightarrow (V_i^{f1}, V_i^{f2}, \ldots, V_i^{fj}, \ldots V_i^{fm})_{scaled}$$

In some embodiments, apparatus 100 may include a localization system. During electrophysiological (EP) procedures cardiologists may insert catheters with electrodes into the heart cavities and/or on the heart's surfaces. Determining the position and orientation of a medical device, such as a catheter, in a human body may be accomplished through various systems. One such system is known as an electrical impedance-based positioning system. Generally, electrical impedance-based positioning systems include one or more pairs of body surface electrodes, a reference sensor, and one or more sensors attached to the medical device. The system may then determine the position and orientation of the medical device by applying a current across pairs of electrodes, measuring respective voltages induced at the medical device sensors, and then processing the measured voltages. Alternatively, one may implement a magnetic field-based positioning system. Generally, magnetic field-based positioning systems include one or more magnetic field generators attached to or placed near the patient bed or other component of the operating environment, and one or more magnetic field detection coils coupled with a medical device. As an alternative, the field generators may be coupled with a medical device, and the detection coils may be attached to or placed near a component of the operating environment. Using the magnetic field produced by the generators and signals produced by the detection coils, the system may process the signals to produce one or more position and orientation readings associated with the coils. Unlike an electrical impedance-based system, where the coordinate system is relative to the patient, a magnetic field-based system has a coordinate system that is independent of the patient.

Both electrical impedance-based positioning systems and magnetic field-based positioning systems have their advantages. For example, electrical impedance-based positioning systems provide the ability to simultaneously locate a relatively large number of sensors on multiple medical devices. However, because electrical impedance-based positioning systems employ electrical current flow in the human body, such systems may be subject to electrical interference and are thus less precise. As a result, geometries and representations may appear distorted relative to actual images of subject regions of interest. On the other hand, magnetic field-based positioning systems are not dependent on characteristics of the patient's anatomy and typically provide improved accuracy in comparison. However, magnetic field-based positioning systems are generally limited to tracking relatively fewer sensors in comparison to electrical impedance-based positioning systems and are typically costlier.

In some embodiments, localization system may include a magnetic sensor. A "magnetic sensor" is a device that detects and measures magnetic fields. Such sensors may determine the strength, direction and/or in some embodiments the rate of change of a magnetic field. Exemplary embodiments of magnetic sensors may include magnetoresistive sensors, hall effect sensors, fluxgate sensors, magnetic resonance imaging (MRI)-compatible sensors, and/or the like. As used throughout this disclosure, "position data" refers to the specific location and orientation of the catheter. Position data 144 may include spatial coordinates, orientation, distance, alignment, and/or the like. Further, spatial coordinates may include x, y, z coordinates in three-dimensional space and/or polar coordinates for spherical or cylindrical setups. Orientation may include the angle and/or positioning of the electrode in relation to other components or the medium with which it is interacting with. For example, and without limitation, the angle of inclination or rotation relative to a reference plane. Further, distance may be measured from a fixed point or other reference electrodes. For example, the distance from a reference electrode and/or the distance from the magnetic sensor. In some embodiments, potential signals from on or more electrodes may be used to located said electrodes relative to the magnetic sensor.

With continued reference to FIG. 1, the normalized potential signal 136 may be displayed using a downstream device. As used in this disclosure, a "downstream device" is an electronic device that presents information to the entity. In some cases, downstream device may be configured to project or show visual content generated by computers, video devices, or other electronic mechanisms. In some cases, downstream device may include a liquid crystal display (LCD), a cathode ray tube (CRT), a plasma display, a light emitting diode (LED) display, and any combinations thereof. In a non-limiting example, one or more downstream device may vary in size, resolution, technology, and functionality. Downstream device may be able to show any data elements and/or visual elements as listed above in various formats such as, textural, graphical, video among others, in either monochrome or color. Downstream device may include, but is not limited to, a smartphone, tablet, laptop, monitor, tablet, and the like. Downstream device may include a separate device that includes a transparent screen configured to display computer generated images and/or information. In some cases, downstream device may be configured to present a graphical user interface (GUI) to a user, wherein a user may interact with a GUI. In some cases, a user may view a GUI through downstream device. Additionally, or alternatively, processor 104 be connected to downstream device. In one or more embodiments, transmitting the normalized potential signal 136 may include displaying the normalized potential signal 136 at downstream device using a visual interface.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

Figure 2:
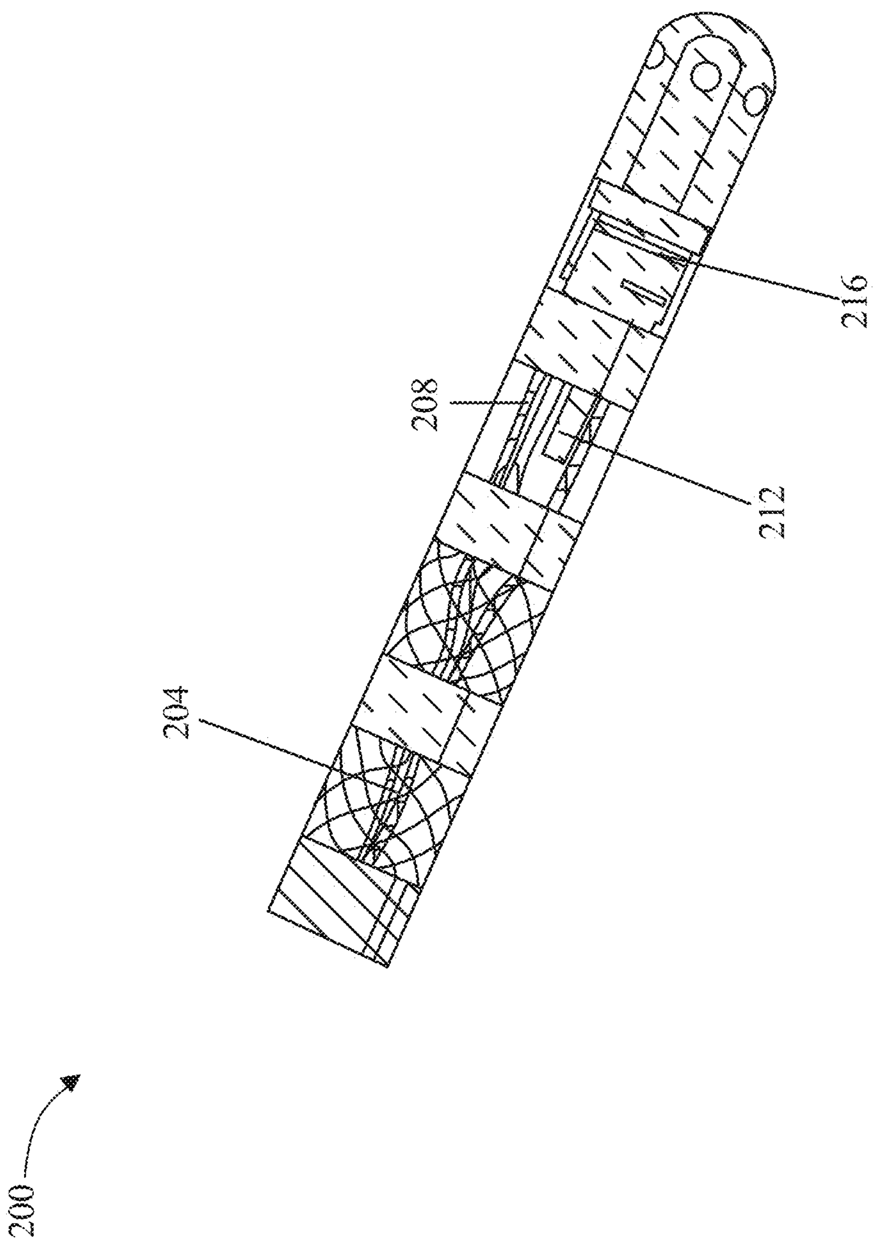
FIG. 2 is an illustration of a 4-electrode catheter comprising a first electrode type and a second electrode type.

Referring now to FIG. 2, an illustration 200 of a four-electrode catheter comprising a first electrode type and a second electrode type. In an embodiment, the four-electrode catheter includes a unique braiding structure 204 located at the distal tip, wherein the distal tip location may increase the shaft pliability compared to the proximal shaft. In an embodiment, the four-electrode catheter includes three fiber optic sensing cables 208. In an embodiment, the four-electrode catheter includes an electrode magnetic sensor 212 for integration with cardiac mapping systems. In an embodiment, the four-electrode catheter includes a contact force sensor 216 located behind the distal tip.

Figure 3:
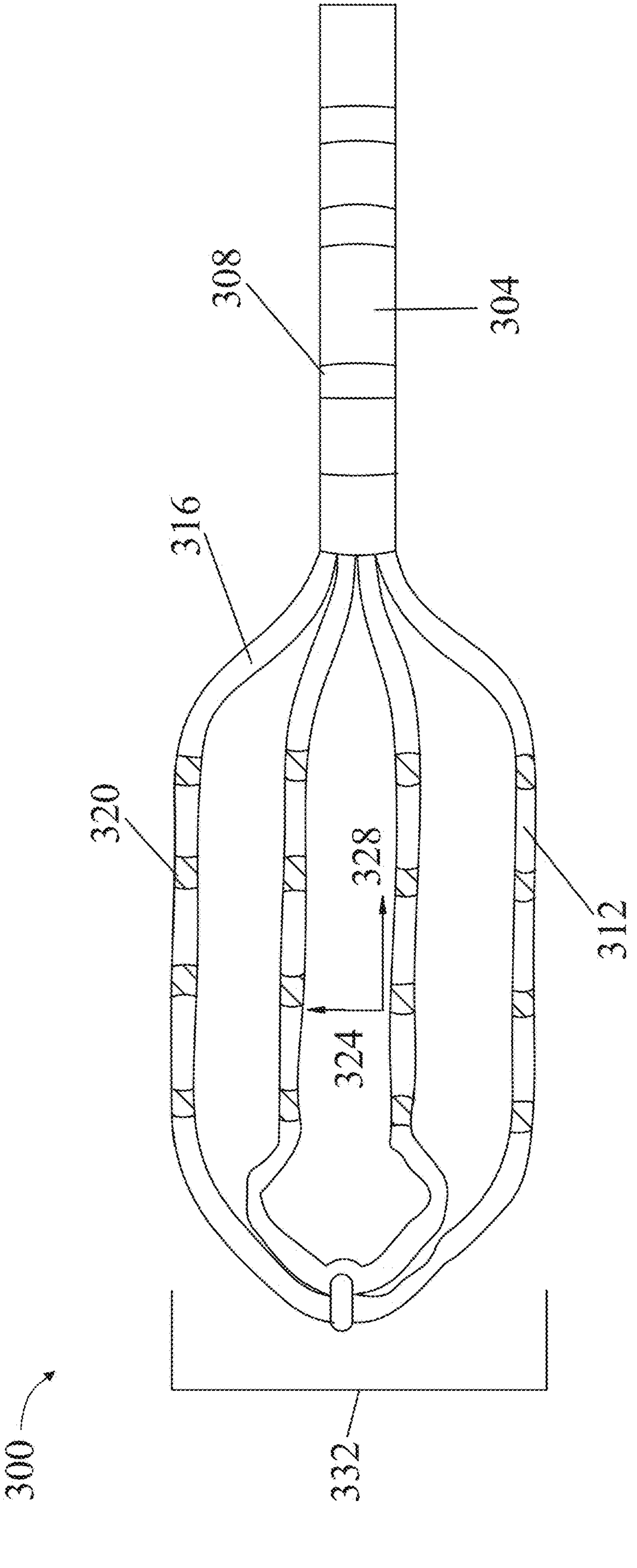
FIG. 3 is an illustration of an 18-electrode catheter comprising a first electrode type and a second electrode type.

Referring now to FIG. 3, an illustration 300 of an 18-electrode catheter comprising a first electrode type and a second electrode type. In an embodiment, the 18-electrode catheter includes a magnetic sensor 304. In an embodiment, the 18-electrode catheter includes one or more shaft electrodes 308. In an embodiment, the one or more shaft electrodes 308 are rigid electrodes. In an embodiment, the 18-electrode catheter includes a flexible part 312. In an embodiment, the 18-electrode catheter includes a spline 316. In an embodiment, the 18-electrode catheter includes one or more grid electrodes 320. In an embodiment, the one or more grid electrodes 320 are flexible electrodes. In an embodiment, the one or more grid electrodes 320 are 1 mm in length. In an embodiment, the one or more grid electrodes 320 are equally spaced along the flexible part 312 of the 18-electrode catheter a vertical distance 324 of 3 mm apart. In an embodiment, the one or more grid electrodes 320 are equally spaced along the flexible part 312 of the 18-electrode catheter a horizontal distance 328 of 3 mm apart. In an embodiment, the grid 332 comprises a plurality of the one or more grid electrodes 320.

Referring now to FIG. 4, an illustration 400 of a diagram of a transducer with a rigid part, a flexible part, a magnetic sensor, a first electrode type, and a second electrode type. In an embodiment, the flexible part 404 includes one or more of a first electrode type 408. In an embodiment, the rigid part 412 includes one or more of a second electrode type 416. In an embodiment, the flexible part 404 may bend as illustrated by the bending action 420. In an embodiment, the transducer includes a magnetic sensor (MS) 424.

Referring now to FIG. 5A, an illustration 500*a* of an 18-electrode catheter in an unbent configuration including a first electrode type and a second electrode type. In an embodiment, the 18-electrode catheter includes a first electrode type 504. In an embodiment, the 18-electrode catheter includes a second electrode type 508.

Figure 5B:
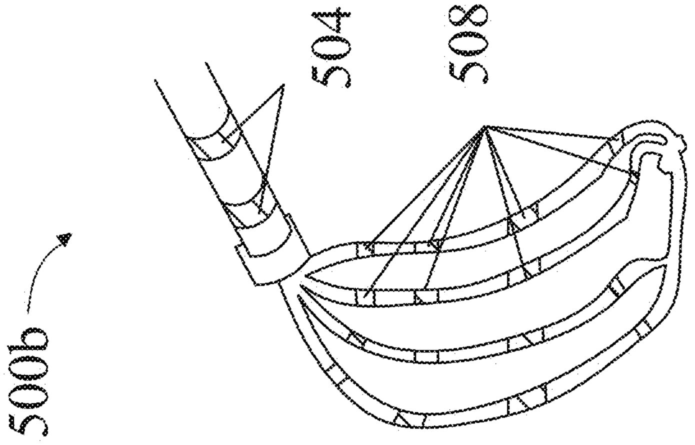
FIG. 5B is an illustration of an 18-electrode catheter in a bent configuration including a first electrode type and a second electrode type.
Figure 5A:
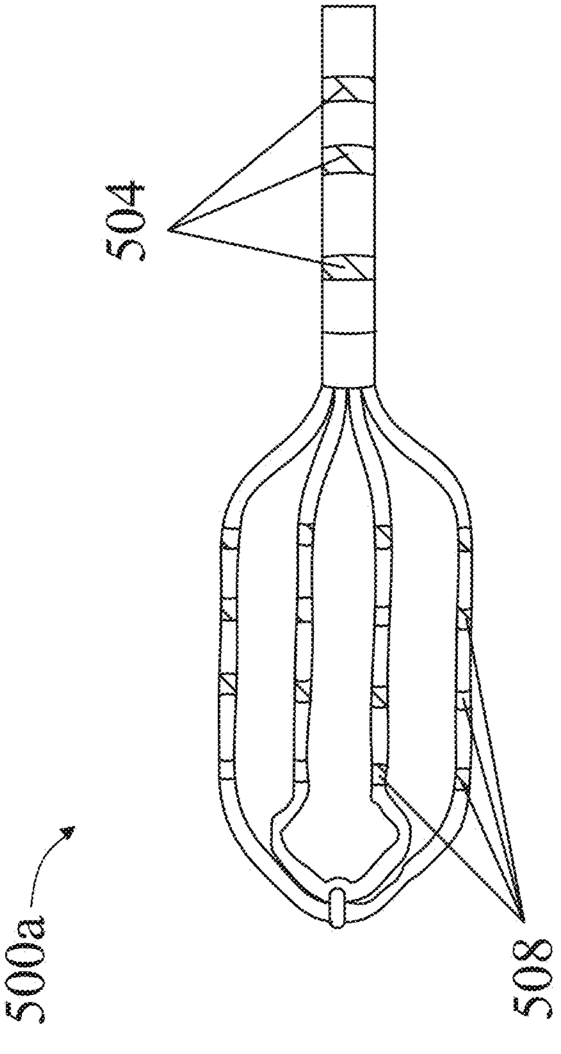
FIG. 5A is an illustration of an 18-electrode catheter in an unbent configuration including a first electrode type and a second electrode type.

Referring now to FIG. 5B, an illustration 500 b of an 18-electrode catheter in a bent configuration including a first electrode type and a second electrode type. In an embodiment, the 18-electrode catheter includes a first electrode type 504. In an embodiment, the 18-electrode catheter includes a second electrode type 508.

Figure 6:
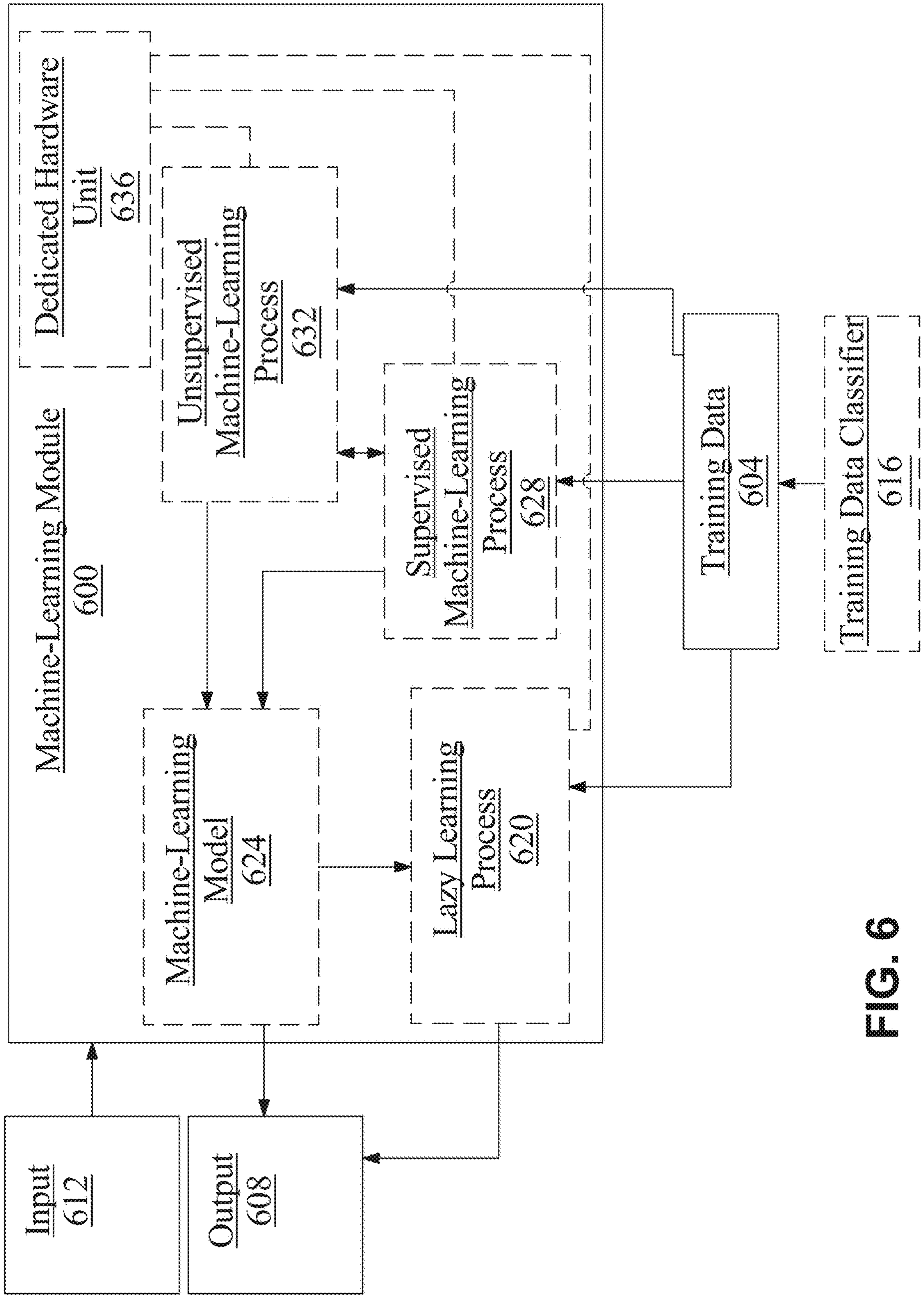
FIG. 6 is a block diagram of an exemplary machine-learning process.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm instantiated in hardware or software logic, data structures, and/or functions that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example inputs may include a plurality of potential signals from various electrode types and the output may include a normalized potential signal.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to categories related to electrode type, tissue type, and the like.

Still referring to FIG. 6, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)P(A)\div P(B)$, where $P(A/B)$ is the probability of hypothesis A given data B also known as posterior probability; $P(B/A)$ is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 6, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 6, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 6, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 6, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 6, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 6, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 6, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 6, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 6, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 6, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or Feature scaling may include mean normalization, which subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include a plurality of potential signals from various electrode types as described above as inputs, a normalized potential signal as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

With further reference to FIG. 6, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 6, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 632 may not require a response variable; unsupervised processes 632 may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 6, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 6, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 6, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 6, one or more processes or algorithms described above may be performed by at least a dedicated hardware unit 636. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 636 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 636 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 636 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 7:
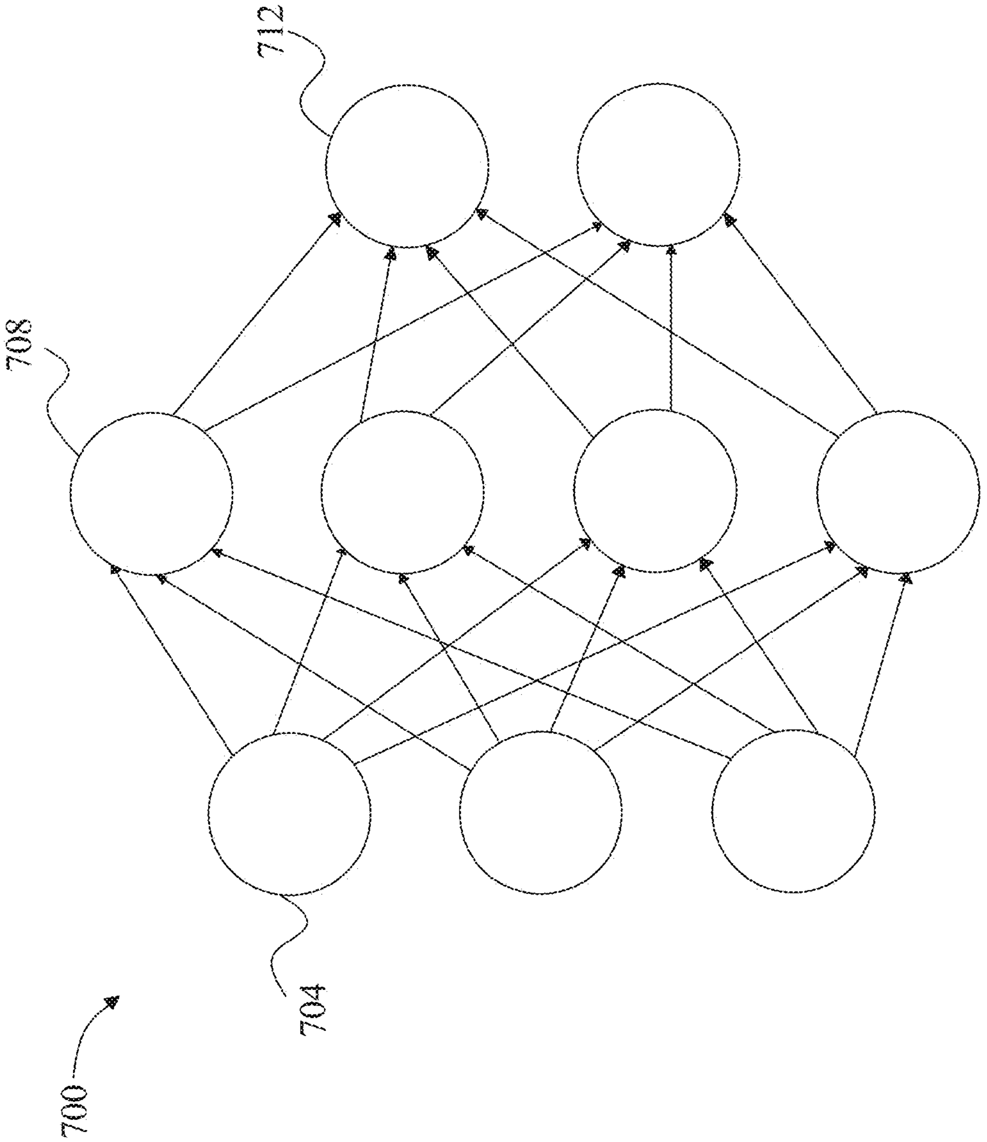
FIG. 7 is a diagram of an exemplary embodiment of a neural network.

Referring now to FIG. 7, an exemplary embodiment of neural network 700 is illustrated. A neural network 700 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 704, one or more intermediate layers 708, and an output layer of nodes 712. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 8:
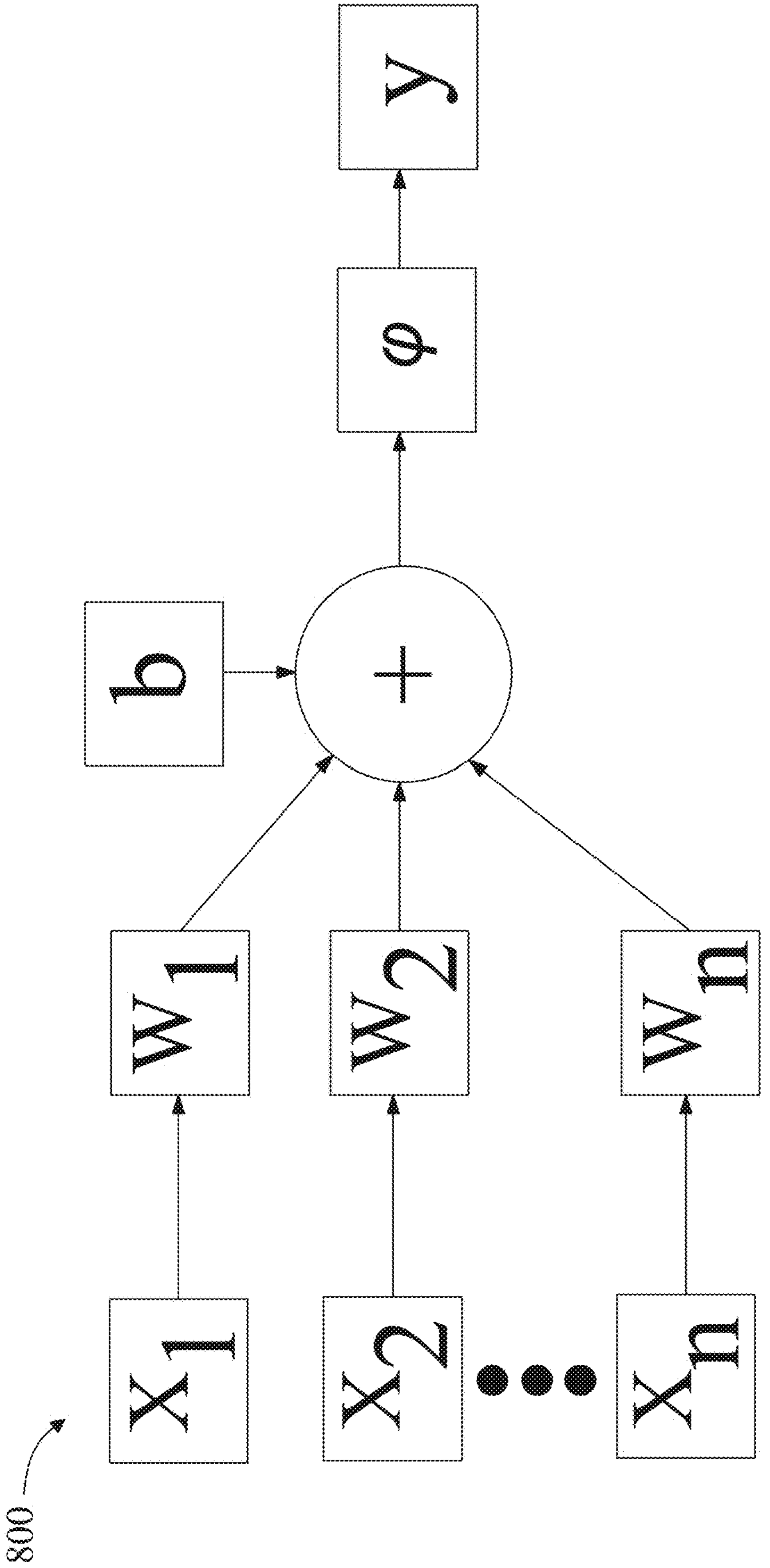
FIG. 8 is a diagram of an exemplary embodiment of a node of a neural network.

Referring now to FIG. 8, an exemplary embodiment of a node 800 of a neural network is illustrated. A node may include, without limitation, a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tan h^2(x)$, a rectified linear unit function such as $f(x)=\max(0,x)$, a "leaky" and/or "parametric" rectified linear unit function such as $f(x)=\max(ax,x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tan h(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs x; that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 9:
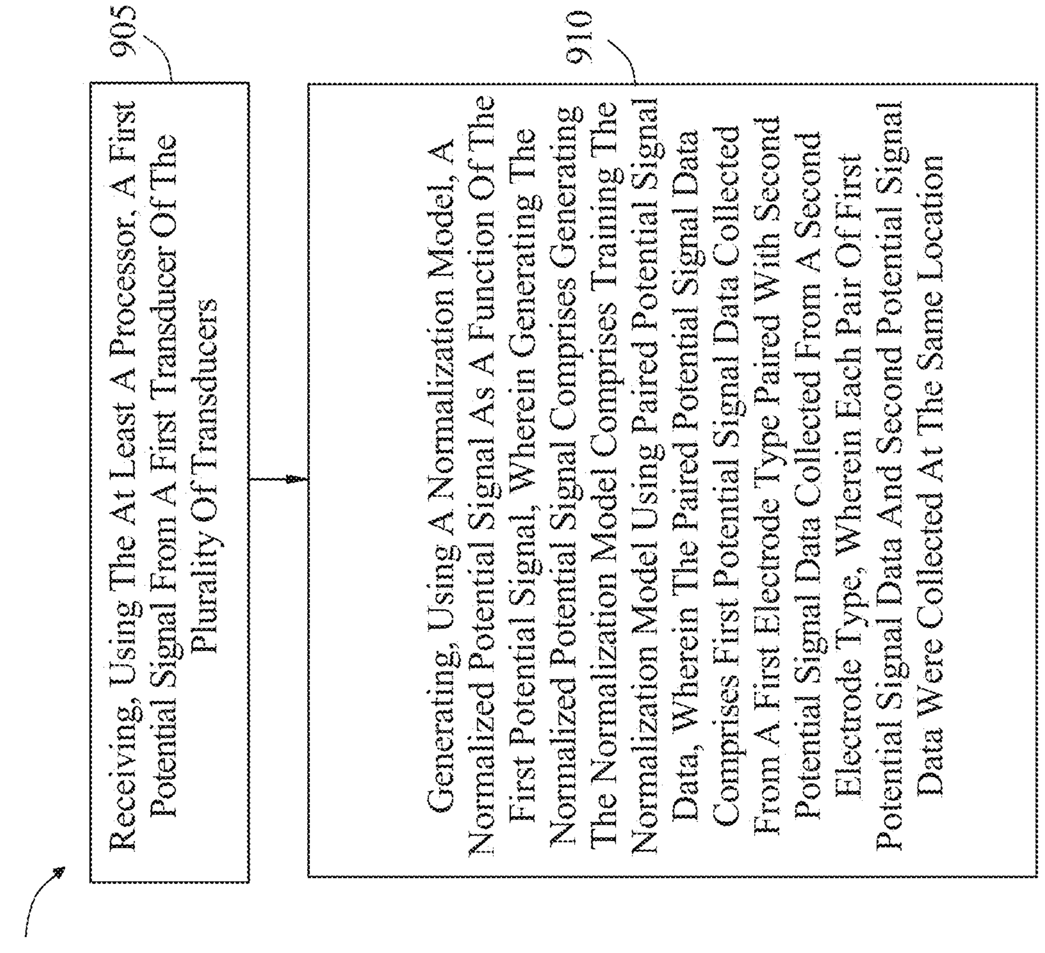
FIG. 9 is a block diagram of an exemplary method for determining a normalized voltage across non-identical electrodes.

Referring now to FIG. 9, a flow diagram of an exemplary method 900 for determining a normalized voltage across non-identical electrodes is illustrated. At step 905, method 900 includes receiving, using the at least a processor, the first potential signal from a first transducer of a plurality of transducers. This may be implemented as described and with reference to FIGS. 1-8.

Still referring to FIG. 9, at step 910, method 900 includes generating, using a normalization model, a normalized potential signal as a function of the first potential signal, wherein generating the normalized potential signal comprises generating the normalization model comprises training the normalization model using paired potential signal data, wherein the paired potential signal data comprises first potential signal data collected from a first electrode type paired with second potential signal data collected from a second transducer having a second electrode type, wherein each pair of first potential signal data and second potential signal data were collected at the same location. This may be implemented as described and with reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
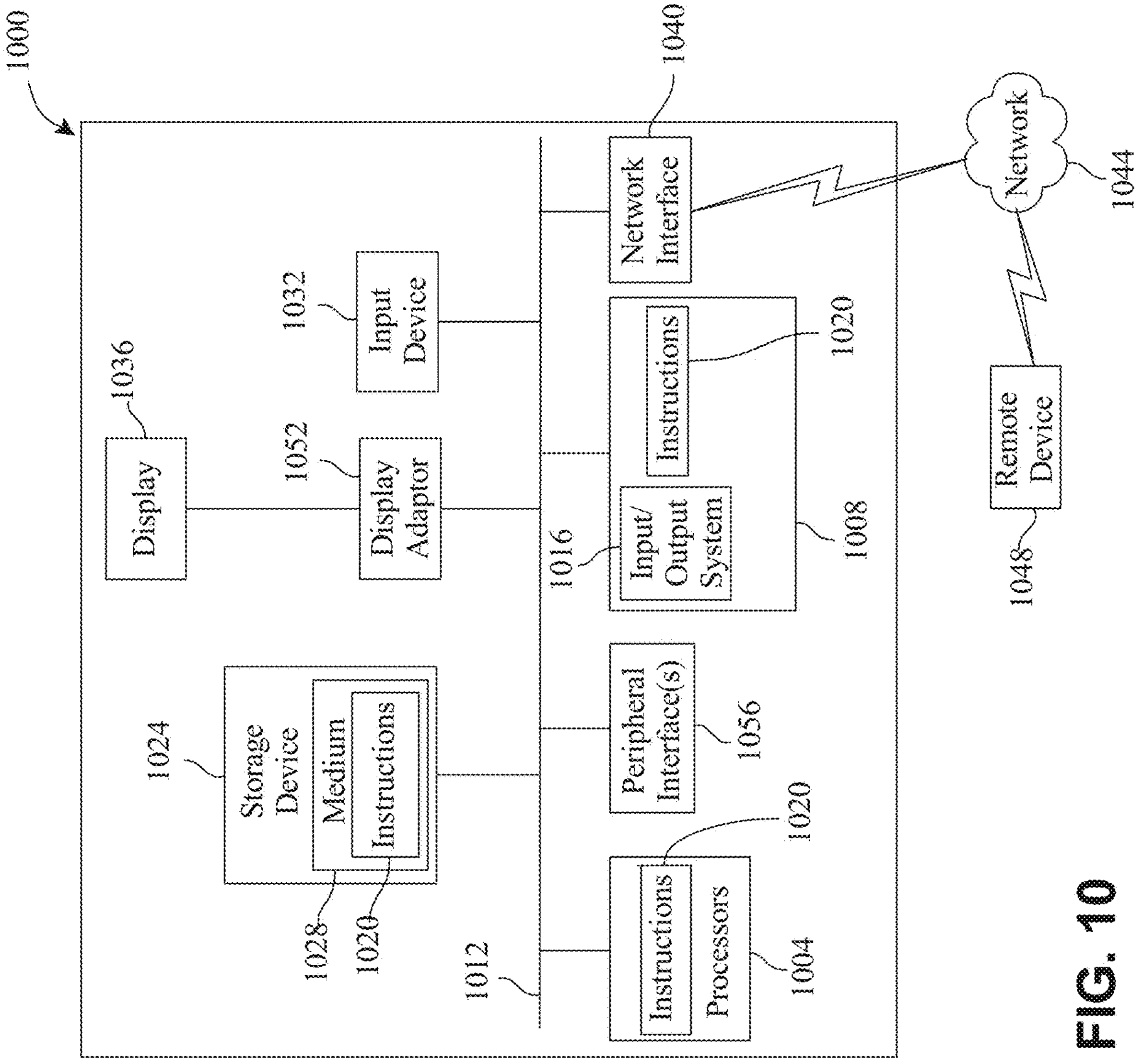
FIG. 10 is a block diagram of a computing system that can be used to implement any one or more of the methodologies disclosed herein and any one or more portions thereof. The drawings are not necessarily to scale and may be illustrated by phantom lines, diagrammatic representations and fragmentary views. In certain instances, details that are not necessary for an understanding of the embodiments or that render other details difficult to perceive may have been omitted.

FIG. 10 shows a diagrammatic representation of one embodiment of computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display device 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for determining a normalized voltage across non-identical electrodes, wherein the apparatus comprises:

a first transducer of a plurality of transducers having a first electrode type and configured to detect bioelectrical activity and output a first potential signal, as a function of the bioelectrical activity; and at least a computing device, wherein the computing device comprises:

a memory; and at least a processor communicatively connected to the memory, wherein the memory contains instructions configuring the at least a processor to:

receive, using the at least a processor, the first potential signal from the first transducer of the plurality of transducers;

locate, using a localization system, a plurality of electrodes, wherein the localization system comprises one or more body surface electrodes and at least a reference sensor;

determine, using the localization system, position data for each electrode type of the plurality of electrodes, wherein the position data comprises an orientation of each electrode of the plurality of electrodes;

generate, using a normalization model, a normalized potential signal as a function of the first potential signal, wherein the normalized potential signal comprises a transformation of the first potential signal from the first electrode type to a second electrode type and wherein the normalized potential signal comprises the position data of the first potential signal and wherein generating the normalized potential signal comprises generating the normalization model further comprising:

receiving training data, wherein the training data comprises datasets of potential signals collected from a plurality of different electrode types, each with varying characteristics including at least size, shape, material, and placement;

training, iteratively, the normalization model using the training data, wherein training the normalization model includes retraining the normalization model with feedback from previous iterations of the normalization model; and generating the normalization model using paired potential signal data, wherein generating the normalization model comprises using the position data with the first potential signal to generate the normalized potential signal, wherein the paired potential signal data comprises first potential signal data collected from the first electrode type paired with second potential signal data collected from the second electrode type, wherein each pair of the first potential signal data and the second potential signal data were collected at a same location; and receive user input, wherein the user input comprises user feedback, and wherein the user feedback is configured to further refine the normalization model in real-time.

2. The apparatus of claim 1, wherein the first transducer of the plurality of transducers comprises an intramuscular electrode.

3. The apparatus of claim 2, wherein the apparatus further comprises at least a catheter configured for intramuscular use, wherein the at least a catheter is coupled to the intramuscular electrode.

4. The apparatus of claim 2, wherein the first potential signal comprises electrogram (EGM) signals collected from the intramuscular electrode.

5. The apparatus of claim 1, wherein the normalization model comprises a regression model.

6. The apparatus of claim 1, wherein the paired potential signal data comprises Fast Fourier Transform (FFT) voltage data.

7. The apparatus of claim 1, wherein the normalization model is configured to calculate a first FFT voltage value for a plurality of voltages of the first potential signal across a plurality of frequencies of the first electrode type.

8. The apparatus of claim 7, wherein the normalization model is further configured to:

generate, using the normalization model, a FFT voltage value from the second electrode type across the plurality of frequencies of the second electrode type corresponding to the first FFT voltage value; and output a second FFT voltage value for the second electrode type.

9. The apparatus of claim 1, wherein the normalization model comprises a machine learning model.

10. The apparatus of claim 1, wherein the normalized potential signal is displayed using a downstream device.

11. A method for determining a normalized voltage across non-identical electrodes, wherein the method comprises:

receiving, using at least a processor, a first potential signal from a first transducer of a plurality of transducers;

locating, using a localization system, a plurality of electrodes, wherein the localization system comprises one or more body surface electrodes and at least a reference sensor;

determining, using the localization system, position data for each electrode type of the plurality of electrodes, wherein the position data comprises an orientation of an electrode;

generating, using a normalization model, a normalized potential signal as a function of the first potential signal, wherein the normalized potential signal comprises a transformation of the first potential signal from a first electrode type to a second electrode type and wherein the normalized potential signal comprises the position data of the first potential signal and wherein generating the normalized potential signal comprises generating the normalization model comprising:

receiving training data, wherein the training data comprises datasets of potential signals collected from a plurality of different electrode types, each with varying characteristics including at least size, shape, material, and placement;

training, iteratively, the normalization model using the training data, wherein training the normalization model includes retraining the normalization model with feedback from previous iterations of the normalization model; and generating the normalization model using paired potential signal data, wherein generating the normalization model comprises using the position data with the first potential signal to generate the normalized potential signal, wherein the paired potential signal data comprises first potential signal data collected from the first electrode type paired with second potential signal data collected from the second electrode type, wherein each pair of first potential signal data and second potential signal data were collected at a same location; and receiving user input, wherein the user input comprises user feedback, and wherein the user feedback is configured to further refine the normalization model in real time.

12. The method of claim 11, wherein the first transducer of the plurality of transducers comprises an intramuscular electrode.

13. The method of claim 12, wherein the method further comprises at least a catheter configured for intramuscular use, wherein the at least a catheter is coupled to the intramuscular electrode.

14. The method of claim 12, wherein the first potential signal comprises electrogram (EGM) signals collected from the intramuscular electrode.

15. The method of claim 11, wherein the normalization model comprises a regression model.

16. The method of claim 11, wherein the paired potential signal data comprises Fast Fourier Transform (FFT) voltage data.

17. The method of claim 11, wherein the normalization model is configured to calculate a first FFT voltage value for a plurality of voltages of the first potential signal across a plurality of frequencies of the first electrode type.

18. The method of claim 17, wherein the normalization model is further configured to:

generate, using the normalization model, a FFT voltage value from the second electrode type across the plurality of frequencies of the second electrode type corresponding to the first FFT voltage value; and output a second FFT voltage value for the second electrode type.

19. The method of claim 11, wherein the normalization model comprises a machine learning model.

20. The method of claim 11, wherein the normalized potential signal is displayed using a downstream device.

* * * * *